US005970974A

United States Patent [19]

Van Der Linden et al.

[11] Patent Number: 5,970,974

[45] Date of Patent: *Oct. 26, 1999

[54] DOSATING UNIT FOR AN ULTRASONIC ATOMIZER DEVICE

[75] Inventors: Klaus Van Der Linden, Redwitz-Unterlangenstadt; Olaf Haack, Staffelstein; Martin Rüttel, Grub, all of Germany; Brindra-Paul Singh-Chawla, Nottingham, United Kingdom

[73] Assignee: Siemens Aktiengesellschaft, Germany

[ * ] Notice: This patent is subject to a terminal disclaimer.

[21] Appl. No.: 08/913,247

[22] PCT Filed: Mar. 14, 1996

[86] PCT No.: PCT/EP96/01092

§ 371 Date: Sep. 10, 1997

§ 102(e) Date: Sep. 10, 1997

[87] PCT Pub. No.: WO96/28205

PCT Pub. Date: Sep. 19, 1996

[30] Foreign Application Priority Data

| | | | |
|---|---|---|---|
| Mar. 14, 1995 | [DE] | Germany | 195 09 193 |
| Mar. 14, 1995 | [DE] | Germany | 195 09 194 |

[51] Int. Cl.[6] .................. A24D 1/04

[52] U.S. Cl. .................. 128/200.16; 128/200.14

[58] Field of Search .................. 128/200.16, 200.18, 128/200.14, 200.21, 203.12

[56] References Cited

U.S. PATENT DOCUMENTS

| | | | |
|---|---|---|---|
| 2,734,504 | 2/1956 | Crescas et al. | 128/218 |
| 3,390,815 | 7/1968 | Kavan et al. | 222/137 |
| 3,392,916 | 7/1968 | Engström et al. | 239/102 |

(List continued on next page.)

FOREIGN PATENT DOCUMENTS

| | | |
|---|---|---|
| 0531640 | 12/1957 | Belgium . |
| 2152747 | 12/1995 | Canada . |
| 0004039 | 9/1979 | European Pat. Off. . |

(List continued on next page.)

OTHER PUBLICATIONS

Zierenberg, "The Respimat, A New Inhalation System Based on the Piezoelectric Effect", Journal of Biopharmaceutical Sciences, 3(½), 1992, pp. 85–90.

*Primary Examiner*—John G. Weiss
*Assistant Examiner*—Charles W. Anderson
*Attorney, Agent, or Firm*—David M. Quinlan, P.C.

[57] ABSTRACT

The invention relates to an ultrasonic atomizer device (2) for a fluid (60), in particular a bronchospasmolytic agent, in which a propelling element (10) operable by an electronic circuit (6) to deliver the fluid to an atomization surface (28) that is also supplied with ultrasound waves from the electronic circuit (6) is provided in a housing (4), the propelling element (10) having a coupling member (32) which is meshing with a further coupling member (34) of a replaceable dosating unit (14) for transferring propelling power to the dosating unit (14) to effect a linear movement (68) of a piston (66) arranged in an ampoule (28) within the dosating unit (14). The invention also relates to a system comprising a device (2) as described and a dosating unit (14) inserted into that device (2).

24 Claims, 12 Drawing Sheets

U.S. PATENT DOCUMENTS

| | | | |
|---|---|---|---|
| 3,415,419 | 12/1968 | Jewett et al. | 222/76 |
| 3,720,211 | 3/1973 | Kyrias | 128/218 A |
| 3,738,574 | 6/1973 | Guntersdorfer et al. | 239/102 |
| 3,812,843 | 5/1974 | Wootten et al. | 128/2 R |
| 3,812,854 | 5/1974 | Michaels et al. | 128/194 |
| 4,094,317 | 6/1978 | Wasnich | 128/194 |
| 4,109,863 | 8/1978 | Olson et al. | 239/102 |
| 4,113,809 | 9/1978 | Abair et al. | 261/81 |
| 4,128,407 | 12/1978 | Chapel | 55/259 |
| 4,155,490 | 5/1979 | Glenn | 222/327 |
| 4,191,187 | 3/1980 | Wright | 128/218 A |
| 4,196,730 | 4/1980 | Wilson | 128/214 |
| 4,294,407 | 10/1981 | Reichl et al. | 239/102 |
| 4,300,546 | 11/1981 | Kruber | 128/200.16 |
| 4,334,531 | 6/1982 | Reichl et al. | 128/200.14 |
| 4,351,332 | 9/1982 | Whitney et al. | 128/214 F |
| 4,407,659 | 10/1983 | Adam | 604/155 |
| 4,417,889 | 11/1983 | Choi | 604/246 |
| 4,585,439 | 4/1986 | Michel | 604/155 |
| 4,657,027 | 4/1987 | Paulsen | 128/762 |
| 4,689,515 | 8/1987 | Benndorf et al. | 310/316 |
| 4,722,734 | 2/1988 | Kolln | 604/151 |
| 4,731,058 | 3/1988 | Doan | 604/155 |
| 4,749,109 | 6/1988 | Kamen | 222/333 |
| 4,790,479 | 12/1988 | Matsumoto et al. | 239/102.2 |
| 4,793,339 | 12/1988 | Matsumoto et al. | 128/200.16 |
| 4,877,989 | 10/1989 | Drews et al. | 310/323 |
| 4,883,472 | 11/1989 | Michel | 604/208 |
| 4,888,516 | 12/1989 | Daeges et al. | 310/323 |
| 4,912,357 | 3/1990 | Drews et al. | 310/323 |
| 4,969,874 | 11/1990 | Michel et al. | 604/140 |
| 4,976,259 | 12/1990 | Higson et al. | 128/200.18 |
| 5,134,993 | 8/1992 | van der Linden et al. | 128/200.14 |
| 5,221,025 | 6/1993 | Privas | 222/1 |
| 5,347,998 | 9/1994 | Hodson et al. | 128/200.23 |
| 5,515,842 | 5/1996 | Ramseyer et al. | 128/200.18 |

FOREIGN PATENT DOCUMENTS

| | | |
|---|---|---|
| 0143895 | 6/1985 | European Pat. Off. . |
| 0258637 | 3/1988 | European Pat. Off. . |
| 0362484 | 4/1990 | European Pat. Off. . |
| 0373237 | 6/1990 | European Pat. Off. . |
| 0526824 | 2/1993 | European Pat. Off. . |
| 0557553 | 9/1993 | European Pat. Off. . |
| 0567186 | 10/1993 | European Pat. Off. . |
| 0569611 | 11/1993 | European Pat. Off. . |
| 0618426 | 3/1994 | European Pat. Off. . |
| 0642802 | 3/1995 | European Pat. Off. . |
| 0657226 | 6/1995 | European Pat. Off. . |
| 0689879 | 1/1996 | European Pat. Off. . |
| 2285930 | 4/1976 | France . |
| 2444504 | 7/1980 | France . |
| 1103522 | 3/1961 | Germany . |
| 2107310 | 8/1971 | Germany . |
| 2524862 | 12/1975 | Germany . |
| 2934732 | 2/1981 | Germany . |
| 3244836 | 6/1984 | Germany . |
| 3339180 | 5/1985 | Germany . |
| 3428655 | 2/1986 | Germany . |
| 3508560 | 9/1986 | Germany . |
| 3625461 | 2/1988 | Germany . |
| 3841442 | 6/1990 | Germany . |
| 4034025 | 4/1992 | Germany . |
| 4107479 | 9/1992 | Germany . |
| 686872 | 7/1996 | Switzerland . |
| 1434746 | 5/1976 | United Kingdom . |
| 2099710 | 12/1982 | United Kingdom . |
| 8905407 | of 1989 | United Kingdom . |
| 2262452 | 6/1993 | United Kingdom . |
| 2272389 | 5/1994 | United Kingdom . |
| 9411624 | 9/1994 | United Kingdom . |
| 9211050 | 7/1992 | WIPO . |
| 9302720 | 2/1993 | WIPO . |
| 9312823 | 7/1993 | WIPO . |
| WO 94/09912 | 5/1994 | WIPO . |
| 9416759 | 8/1994 | WIPO . |
| 9628205 | 9/1996 | WIPO . |
| 9628206 | 9/1996 | WIPO . |

DOSATING UNIT FOR AN ULTRASONIC ATOMIZER DEVICE

BACKGROUND OF THE INVENTION

1. Field of the Invention

The present invention relates to the atomization of a liquid, and more particularly, to an inhaler device with a removable dosating unit for delivering precise amounts of medicament to an ultrasonic atomizer device for atomizing the medicament for inhalation by a patient.

2. Description of the Prior Art

Liquid atomizers are well known and come in several types, including aerosol, manual and ultrasonic. For example, there are aerosol atomizers for various applications, such as dispensing cosmetic and hygienic products (hair spray, deodorant, etc.) and cleaning solutions (disinfectants, air fresheners, etc.). Aerosol atomizers can also be used for dispensing medicaments although they have significant drawbacks when used for that purpose. For one thing, they dispense medicaments at a high velocity, which can adversely affect a patient's ability to coordinate dispensing and inhaling the medicament. Moreover, medicament atomized and dispensed by aerosol is usually very cold and can irritate the patient's throat, and the aerosol propellant may have adverse affects on the patient as well as on the environment.

Manual atomizers are also available. In this type of device, the medicament is dispensed by a manual force provided by the patient to atomize the medicament. The most significant advantage of such atomizers is their simplicity, which makes them capable of being made small enough to be carried by patients and thus be readily available for use at any time.

However, difficulties with purely manual atomizers include non-uniformity of dosage from one patient to another (since different people will inevitably use different amounts of force to operate the device and because such devices sometimes deliver different dosages from one use to another), difficulty in coordinating the required manual actuation and inhalation of the expelled medicament (a problem particularly with very young and very old or infirm patients) and inability to protect the medicament from contamination.

Ultrasonic atomizers include one type using a piezoelectric element to atomize a liquid medicament deposited thereon by manually moving a piston within a cylinder containing the medicament to be atomized. The piston forces the liquid from an outlet in the cylinder, which deposits it onto the piezoelectric atomizer, which in turn is activated as part of the manual medicament-dispensing operation.

Examples of this type of ultrasonic atomizer (using a manually dispensed medicament) are shown in U.S. Pat. No. 4,294,407, U.S. Pat. No. 4,877,989 and U.S. Pat. No. 5,134,993. Although such atomizers are better in some respects than their purely manual counterparts, they do not completely solve the problem of providing a uniform dosage under all conditions and for all patients, and they are limited in the amount of medicament that can be atomized because of power considerations relating to the piezoelectric ultrasonic atomizer.

An ultrasonic atomizer is also proposed in European Patent Application EP 0 689 879 A1.

Another type of ultrasonic atomizer includes a pump to deliver liquid from a reservoir to a piezoelectric vibrator. Examples of this type of device are shown in British Patents No. 1,434,746 and No. 2,099,710 and European Patent Application EP 0 569 611 A1. These devices are capable of better uniformity in the amount of liquid atomized at each actuation, but they still have significant drawbacks as portable medication-delivery systems. For example, the atomizers shown in British Patents No. 1,434,746 and No. 2,099,710 clearly would be difficult to miniaturize sufficiently to make them small enough to carry in a patient's pocket or purse for convenient or, in the case of an asthma sufferer, emergency use. Further, the technique in British Patent No. 2,099,710 for dispensing the liquid to be atomized, by crumpling the liquid container, does not allow sufficient dosage precision because of the unpredictability of exactly how the container will deform.

On the other hand, the atomizer of EP 0 569 611 A1 is specifically designed to be a fully-portable, hand-held atomizer for medicament fluids such as bronchospasmolytic agents used to treat asthma. And while it is a significant advance over previously known devices, it, too, has proven unsuitable for various reasons.

A principal problem is the peristaltic tube pump disclosed in EP 0 569 611 A1 as the mechanism for delivering the medicament liquid to the piezoelectric atomizer. Although it is more precise than prior delivery systems, it still is subject to large variations in the amount of liquid it delivers. This is the result of several factors. One such factor is that any bubbles which form in the tube can significantly affect dosage amounts because those amounts are so small. Second, manufacturing tolerances in the tube diameter can also significantly affect dosage amounts for the same reason. EP 0 569 611 A1 also discloses a spring-valve system for pressurizing the liquid storage container and metering fluid therefrom, instead of the tube pump, but that still does not provide the precision dosing required in many applications, such as in a medical device, and is unduly complicated.

The device in EP 0 569 611 A1 has other drawbacks as well. The dosating system, containing the pump (or the spring-valve system) and medicament reservoir, is fairly large, and when attached to the device forms a significant part of its outside envelope. As such, it is prone to becoming detached when the unit is carried in a pocket or purse. In addition, the dosating system is difficult to seal in a manner that maintains suitable microbiological conditions over long periods. Finally, any medicament remaining after actuation at the end of the tube delivering it to the piezoelectric element will be exposed to the atmosphere until the next actuation, and thus be prone to contamination. Because that potentially contaminated medicament is then atomized and inhaled by the patient in the next actuation, it is necessary to address that issue from the standpoint of patient safety.

In addition, all types of prior ultrasonic atomizers suffer from the problem of being unable efficiently and effectively to atomize sufficient amounts of medication. For example, a piezoelectric element of a certain size can only atomize a given amount of liquid on its surface. If that is a smaller amount than the dosage amount for a particular medicament, then the atomizer will be inherently incapable of performing its intended function as an inhalable-medication delivery system. Making the piezoelectric element larger is a potential solution, but the amount of power required to operate a piezoelectric element at a given frequency increases exponentially as the size of the element increases. Accordingly, the size of the piezoelectric element is perforce limited because the atomizer, to be practicable, must be capable of a significant number of operations using batteries small enough to fit into a pocket-size device.

SUMMARY OF THE INVENTION

Accordingly, it is an object of the present invention to provide a dosating unit for an ultrasonic atomizer device that overcomes the shortcomings of the prior art.

In accordance with one aspect of the invention, a dosating unit that is removably mountable to an atomizing device comprises an elongated first section for accepting therein a container or ampoule containing liquid to be delivered to the atomizing device through a delivery conduit or pipe, and an elongated second section secured to the first section and including a drive mechanism having a pusher member for cooperating with a plunger in the ampoule to cause the plunger to translate within the ampoule to force liquid therein through the liquid delivery pipe, a transmission mechanism for converting rotary motion applied thereto into translating motion applied to said pusher member and a driving member for applying rotary motion from a motor in the device to the transmission mechanism.

In accordance with another aspect of the invention, a dosating unit that is removably mountable to an atomizing device comprises a housing for accepting therein an ampoule containing a liquid to be delivered to the atomizing device, and a housing cover having means for securing the cover to the housing, a fluid delivery pipe having an inlet into which liquid in the ampoule is introduced when the cover is in an operative position on the housing and an outlet for delivering fluid to an atomizing surface of the atomizing device, and positioning means for cooperating with the atomizing device to locate the cover precisely in three orthogonal directions relative to the device, wherein the outlet is precisely located relative to the positioning means so that the outlet will be precisely located proximate the atomizing surface when the cover is in its operative position.

In accordance with a still further aspect of the invention, a dosating unit that is removably mountable to an atomizing device comprises a housing accepted by the atomizing device, an ampoule containing a medicament liquid to be supplied to the device for atomization, the ampoule being contained in the housing, and a housing cover disposed on the housing and having a fluid delivery pipe for piercing the ampoule, the cover including securing means for securing the cover to the housing in a first position wherein the fluid delivery pipe does not pierce the ampoule and a second position wherein the fluid delivery pipe pierces the ampoule.

Those and further objects, features and advantages of the present invention will be apparent from the following detailed description of preferred embodiments of the invention when taken in conjunction with the accompanying drawings in which like reference numerals refer to like features throughout.

DETAILED DESCRIPTION OF PREFERRED EMBODIMENTS OF THE INVENTION

Figure 1:
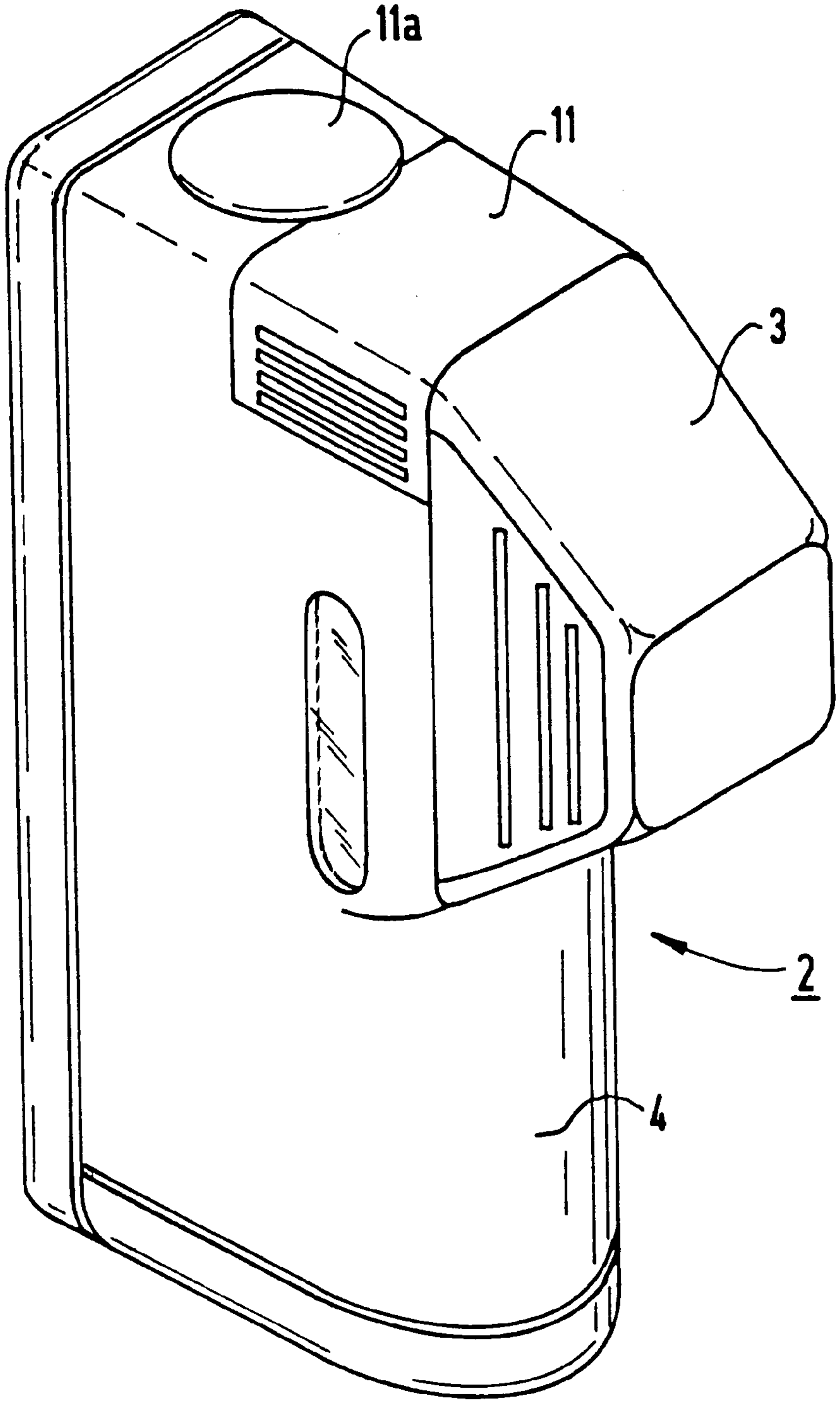
FIG. 1 is a perspective view illustrating an ultrasonic atomizer inhaler device with a cover in a preferred embodiment of the present invention.
Figure 1A:
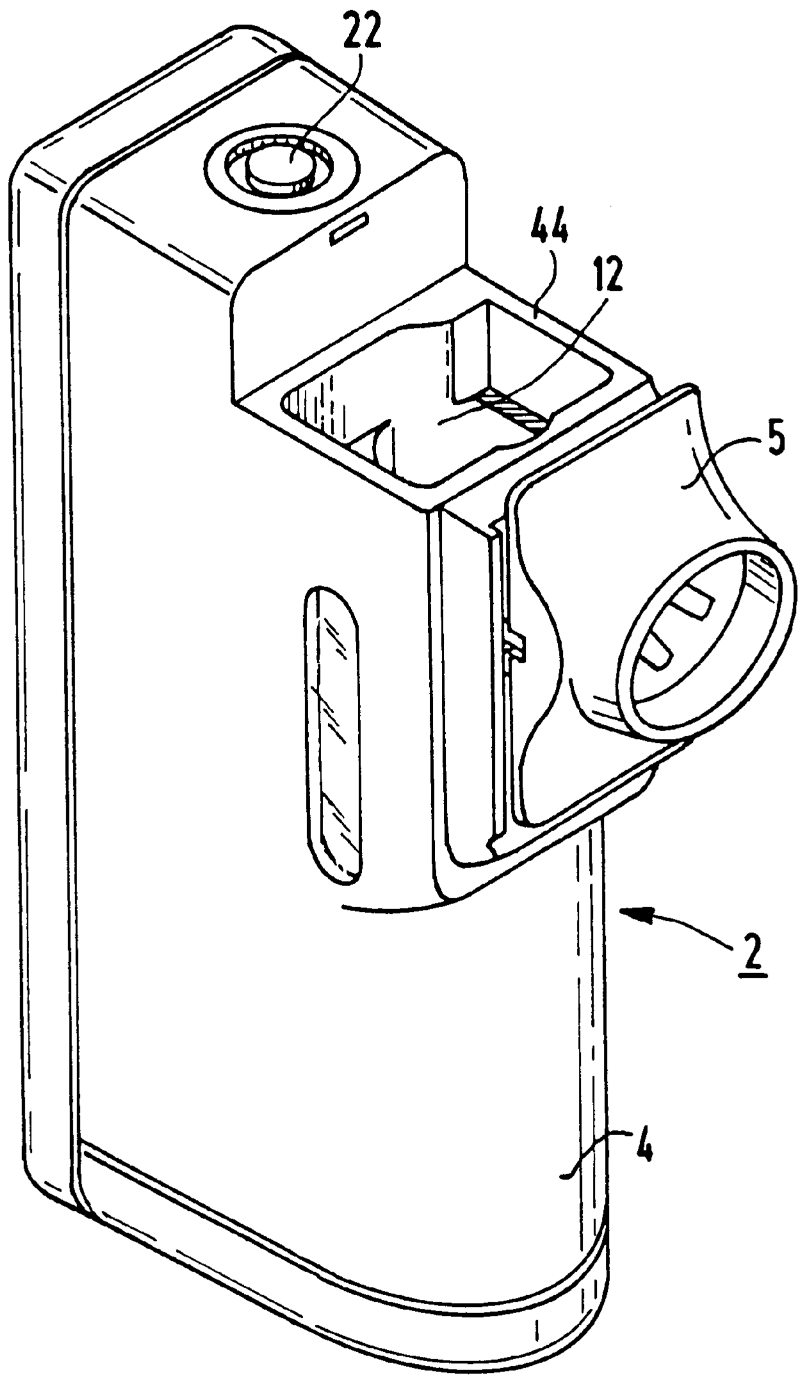
FIG. 1*a* is a perspective view of the device in FIG. 1 with the cover and a blank removed.

As shown in FIGS. 1 and 1A, an inhaler device 2 of the present invention includes a housing 4 to which is attached a mouthpiece 5 from which a patient inhales the medicament atomized by the device 2. The device 2 includes a cover 3 that snaps onto the device over the mouthpiece 5 when the device is not in use. Alternatively, the cover 3 could be hinged to the device at the lower edge of the cover. In such an arrangement the cover would include a suitable latch (not shown), preferably a snap detent (not shown) at its top edge, for example, to hold it in place on the device until the device was to be used. The patient would then swing open the cover about the hinge, and the cover would hang from the hinge, below the patient's chin, as the device was used. The patient would then swing the cover up and back into place over the mouthpiece, and snap it closed for storage.

A recess 12 in the housing 4 accepts a dosating unit 14 according to the present invention. As described in more detail below, an activation element or button 22 initiates operation of the device, whereby a medicament is dispensed by the dosating unit 14 to an atomization surface 28 for inhalation by a patient through the mouthpiece 5, all in a manner that will be described in detail. When the dosating unit 14 is not in place in the recess 12, a blank 11 may be inserted into the recess 12. The blank 11 preferably includes an insert formed of a resilient material (not shown) that forms a friction fit with the walls of the recess to firmly hold the blank 11 in place. A cover 11*a* preferably extends over the activation button 22 when the blank 11 is in place. The blank 11 thus protects the recess 12 from being damaged and prevents unintentional actuation of the device.

Figure 2:
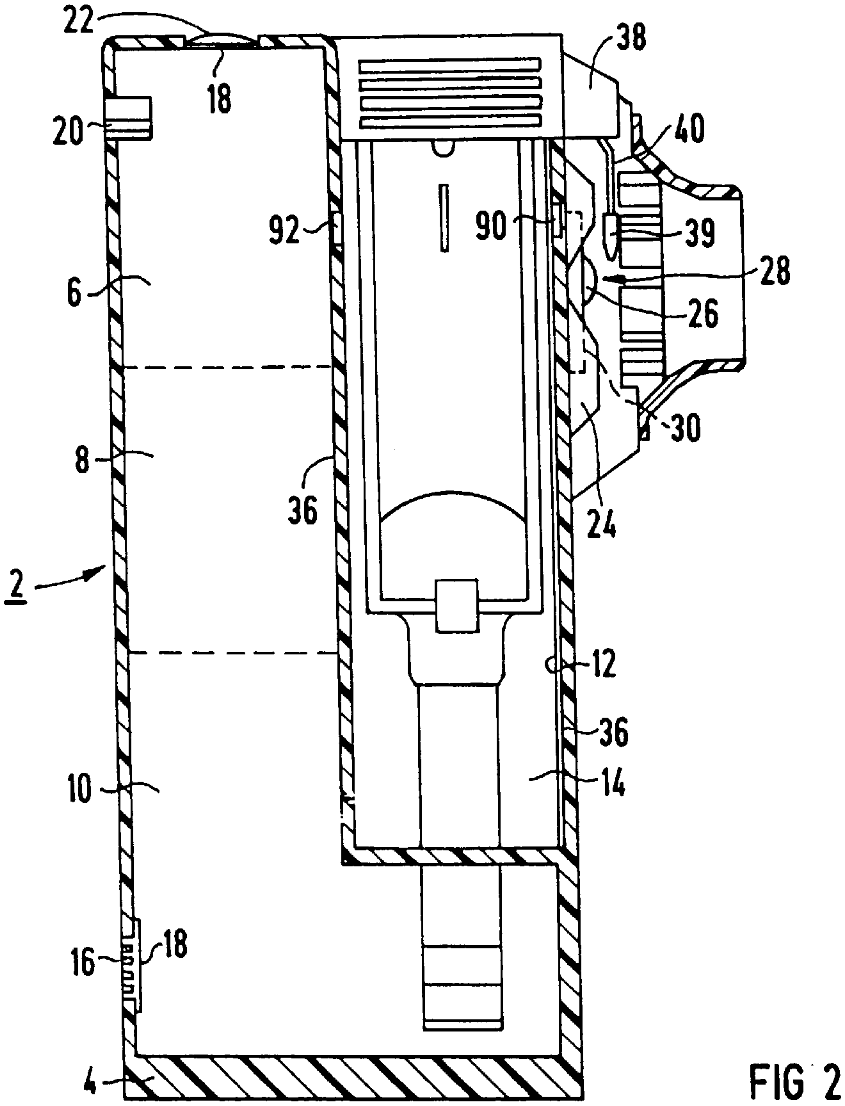
FIG. 2 is a longitudinal partially schematic section through the device in FIG. 1 with the cover and a mouthpiece removed.
Figure 3:
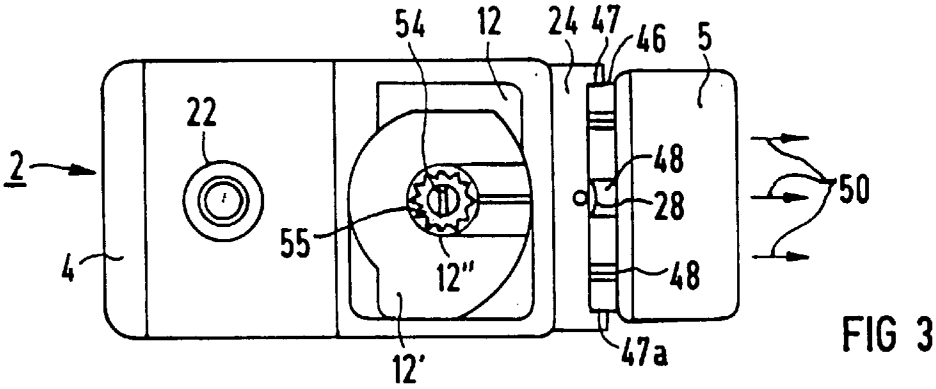
FIG. 3 is a top view of the device in FIG. 1, with the dosating unit of the present invention removed and a mouthpiece in position.

Referring now also to FIGS. 2 and 3 as well as FIGS. 1 and 1A, the housing 4 contains an electronic circuit 6, an accumulator system 8 and a motor 10. In addition, there is a recess 12 in the housing 4 that removably accepts a dosating unit 14, described in detail below. Openings 16 in the housing are preferably covered by a waterproof membrane 18 that is gas and water vapor permeable. A plug-and-socket electrical connector 20 enables the accumulator system 8 to be connected to an external power supply, such as electrical utility current. The accumulator system 8 includes rechargeable batteries and circuitry that recharges the batteries when the connector 20 is connected to utility current.

The openings 16 in housing 4 are preferably lined with a membrane 18 capable of allowing ventilation of gases and vapor but substantially impermeable to water to protect the inner components of the device. The membrane 18 is preferably made of Gore-Tex® material, although other suitable materials may be used. The openings 16 allow ventilation of the housing 4 to permit escape vapor and gases, such as hydrogen gas, for example, which may be formed during a malfunction when charging the batteries of the accumulator system 8.

The activation element or button 22 initiates operation of the device as discussed in detail below. An attachment bracket 24 carries a ceramic piezoelectric element 26, with a button-shaped atomization surface 28, held in a holder 30 secured to the attachment bracket 24. The atomization surface 28 is particularly suitable for the atomization of comparatively small fluid volumes, on the order of 10 $\mu$l to 100 $\mu$l, in 2 sec. to 2.5 sec. The attachment bracket 24 is fixed onto the housing 4 by a suitable mounting (not shown).

The motor 10 has a driving coupling member which meshes with a coupling socket or driven member of the dosating unit assembly 14 for transferring the propelling power of the motor 10 to the dosating unit. The dosating unit 14 comprises a housing 36 closed by a housing cover 38 preferably comprised of molded plastic. A fluid conduit or pipe 40, preferably comprised of a metal, such as steel, is made substantially integral with the housing cover 38 (such as by molding them together) and protrudes from the housing cover 38 at a delivery end preferably terminating in a valve 42 forming a delivery outlet directly adjacent the atomization surface 28. The pipe 40 may alternatively be comprised of a plastic material, such as the material used to form the cover 38.

FIG. 3 is a top view of the pocket inhalator device 2 in FIG. 1, with the dosating unit 14 removed to show the recess 12 in the housing 4 having a shoulder 44 formed on the housing 4. As seen in FIG. 3, the mouthpiece 5 includes attachment tabs 46 that fit into slots 47*a* in flanges 47 on either side of the attachment bracket 24. A flange on the mouthpiece has one or more slots 48 that provide air inlet openings so that a patient can inhale a medicament which has been atomized by the piezoelectric element 26. The air stream and the flow of the atomized medicament are indicated schematically by arrows 50.

It will be appreciated that the mouthpiece 5 forms a chamber around the atomization surface 28, into which chamber a cloud of atomized medicament forms and is then inhaled by a patient who has inserted the mouthpiece into his or her mouth before activating the button 22. It will also be appreciated that the mouthpiece can be replaced or augmented by a mask (not shown) that fits over the nose, or nose and mouth, of a patient.

The driving coupling member accommodated at the bottom of the recess 12 is shown as a propelling gear 55 driven by a shaft 54 operatively connected to the motor 10 for rotation in the direction of the arrow to transfer the propulsive power of the motor 10 to the dosating unit in a manner discussed in more detail below.

Figure 4:
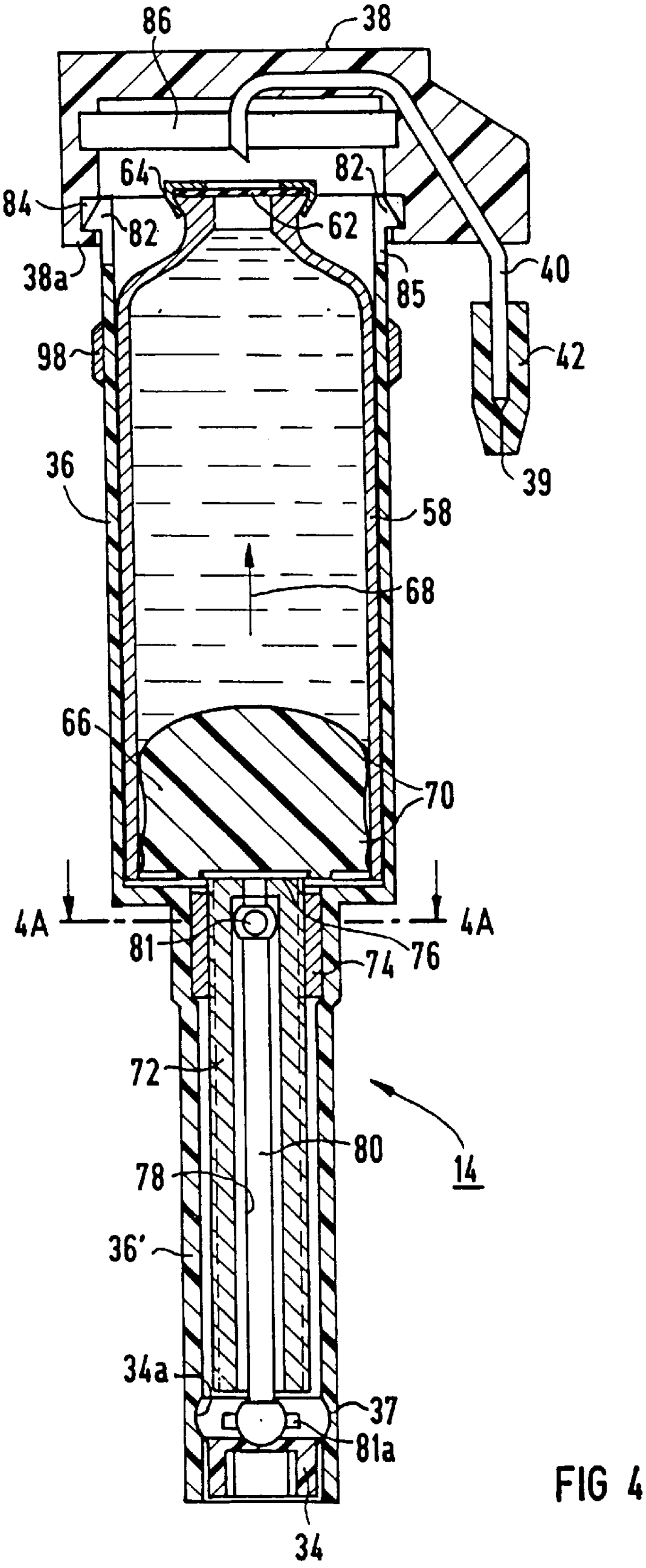
FIG. 4 is a longitudinal sectional view of a preferred embodiment of a dosating unit in accordance with the present invention for the device in FIGS. 1 to 3 in its long-term storage configuration.
Figure 5:
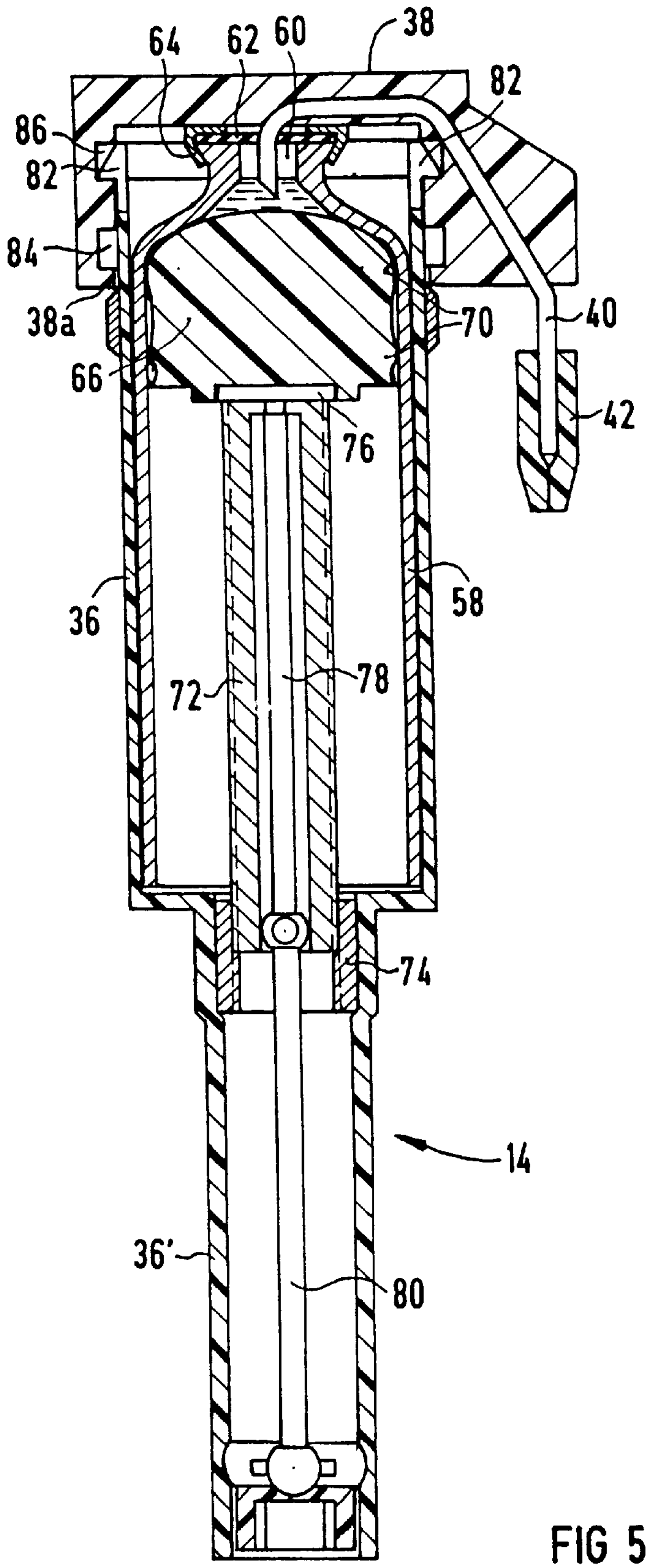
FIG. 5 is a longitudinal sectional the dosating unit for the device in FIGS. 1 to 3 in its operative configuration.
Figure 6:
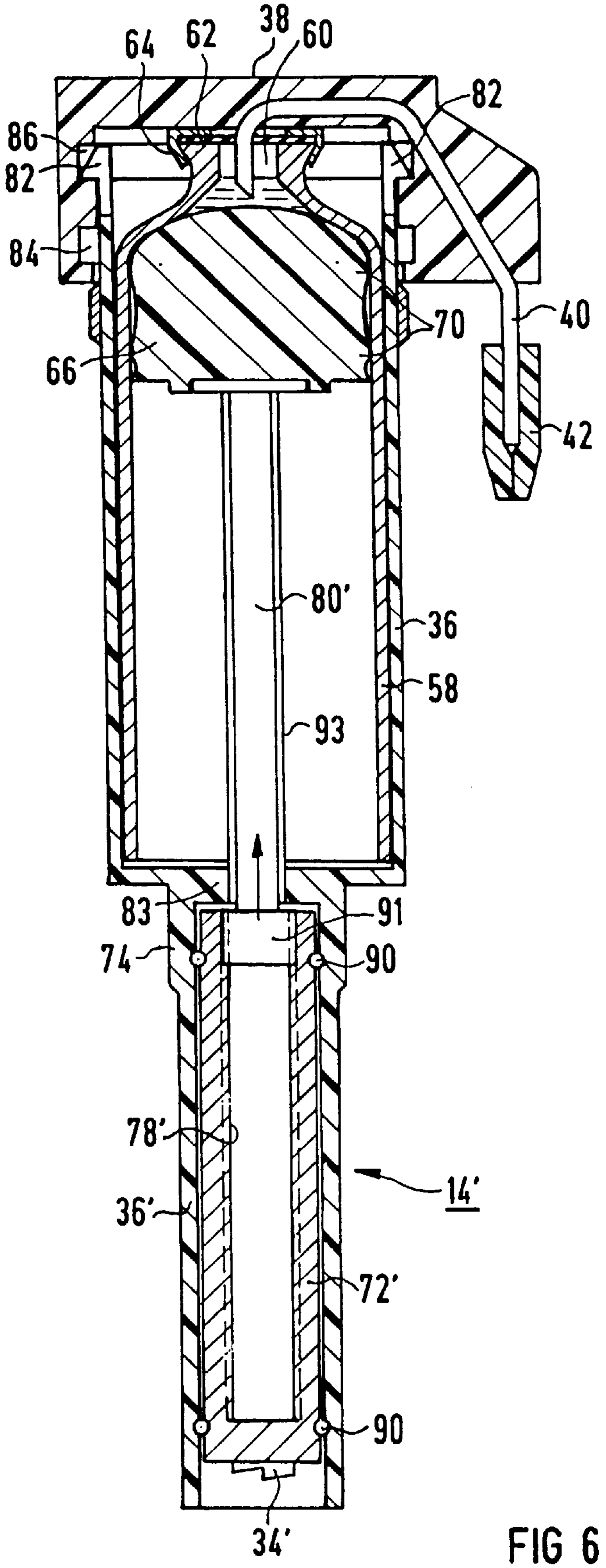
FIG. 6 is a longitudinal view of a second embodiment of a dosating unit in accordance with the present invention for the device in FIGS. 1 to 3 in its operative configuration.

FIGS. 4 to 6 illustrate the removable dosating unit assembly 14 in more detail. The dosating unit housing 36 has an upper section that is preferably an elongated circular cylinder that contains a closely fitting, similarly circularly cylindrical glass ampoule or cartridge 58 filled with the fluid to be atomized, in this case a bronchospasmolytic agent 60. It should be understood that "fluid" as used therein includes solutions, suspensions, emulsions, etc. The glass ampoule 58 has a pierceable lid 62, for example in the form of a rubber diaphragm 62 with flanges sealed to the walls of the ampoule 58. A metal cap 64 on top of the diaphragm 62 holds the diaphragm 62 in place to hermetically seal the cartridge 58 and has a central opening for an inlet end of the fluid pipe 40. A preferably solid piston or plunger 66 comprised of a resilient material, such a rubber is disposed in the cartridge 58 for linear movement in the direction of the arrow 68. The plunger 66 has at least one sealing lip 70 which seals the plunger 66 against the wall of the glass cartridge 58; FIGS. 4 and 5 illustrate a presently preferred embodiment in which two sealing lips 70 are provided on the plunger 66. The top of the plunger 66 is preferably shaped to match the configuration of the glass cartridge 58 at the top, thus maximizing the amount of medicament 60 in the cartridge 58 that is used and concomitantly reducing the amount of unused medicament 60 and thus patient cost.

Figure 6A:
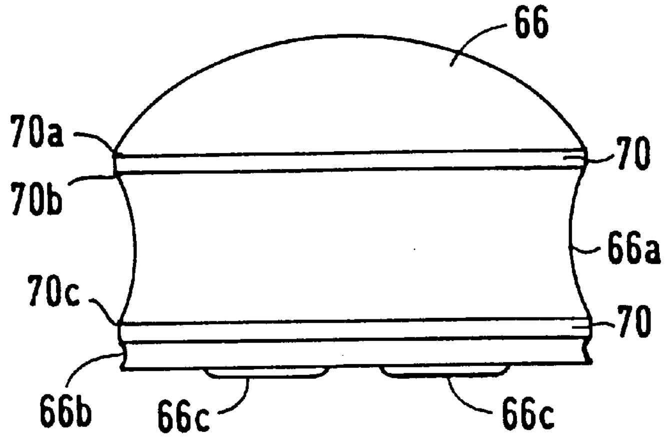
FIGS. 6A and 6B are enlarged elevation and bottom views, respectively, of a dosating unit plunger in accordance with a preferred embodiment of the invention.
Figure 6B:
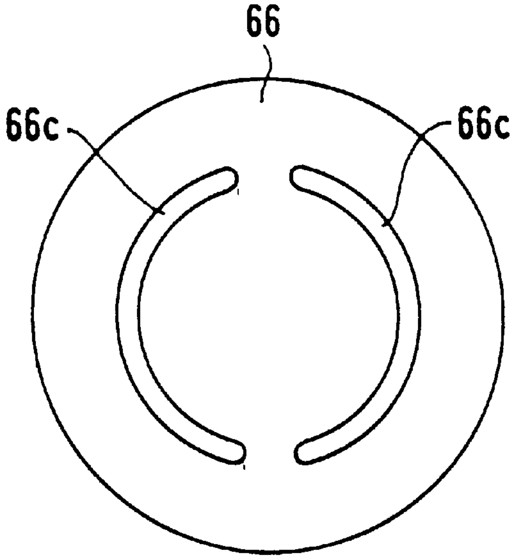

FIGS. 6A and 6B are enlarged elevation and views, respectively, of the dosating unit plunger 66. As seen in FIG. 6A, the profile of the plunger 66 is particularly adapted for use in the dosating unit 14 of the present invention. To that end, each sealing lip 70 is manufactured to tolerances whereby its minimum diameter cannot be less than the maximum allowable inside diameter of the wall of the glass cartridge 58. In other words, even if both the plunger 66 and the glass cartridge 58 are at the limits of their manufacturing tolerances, the sealing lips 70 will still be slightly compressed against the cartridge wall to provide a fluid-tight seal. By the same token, the manufacturing tolerances on the diameters of the sealing lips 70 and inside of the cartridge wall are maintained within sufficiently close limits so that if they are both at the maximum, interference-fit tolerance, friction between them will not be excessive. That friction is also minimized by maintaining the out-of-round tolerances of the sealing lips 70 and cartridge wall as tight as possible consistent with practical cost considerations.

In addition to controlling tolerances, one important feature of one embodiment of the present invention is the provision of slight diameters at the edges 70*a,* 70*b* and 70*c* of the lips 70. These rounded edges further minimize friction between the cartridge walls and the plunger 66. In addition, the plunger 66 is preferably made of rubber, which preferably has Shore Hardness 50–70 and the recessed portion 66*a* between the lips 70 is gradually rounded, in order to maximize the mass and rigidity of the plunger 66 while still providing sufficient sealing contact with the cartridge walls. The lower edge of the plunger 66 is undercut at 66*b,* and a pair of facing arc-shaped rings 66*c* may be provided on the bottom of the plunger 66 to accept between them a plunger pusher 76.

The externally exposed side (that is, the bottom) of the plunger 66 contacts a spindle 72 having an outer thread. The spindle 72 is rotatably arranged in a threaded nut 74 fixed in an elongated reduced-diameter section 36' of the housing 36. Alternatively, the threaded nut 74 may be molded into (not shown) the elongated reduced-diameter section 36' of the housing 36. The spindle 72 includes a plunger pusher plate 76 mounted to rotate freely relative to the spindle 72. The plunger pusher 76 fits relatively central of the plunger 66, preferably between the rings 66*c*.

Figure 4A:
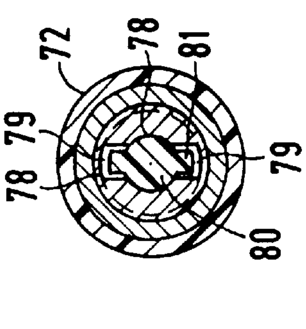
FIG. 4A is transverse sectional view of the spindle and connecting rod portion of the dosating unit in FIG. 4.

The spindle 72 has a central bore 78 that accepts a connecting rod 80. In a preferred embodiment, the central bore 78 has two longitudinal recesses 79 that accept ears 81 on the end of the connecting rod 80, as shown in FIG. 4(A). Thus, rotational movement of the connecting rod 80 is transferred to the spindle 72, while the spindle 72 is free to translate longitudinally relative to the connecting rod 80 as the connecting rod rotates. That is, the connecting rod 80 fits slidingly within the spindle 72. A suitable lubricant system, such as a coating on the mating parts of a silicone lubricant or Teflon® synthetic resin, may be used to facilitate such sliding movement.

The connecting rod 80, itself, is connected to a splined coupling socket 34, such as by ears 81*a* on the rod 80 which engage a channel 34*a* on the coupling socket 34. In one presently preferred embodiment, the coupling socket 34 has a circumferential ridge 34*b* that fits within a circumferential recess 37 in the housing section 36' of the dosating unit 14. The ridge 34*b* and recess 37 form a bearing that permits the coupling socket 34 to rotate relative to the housing section 36' while resisting longitudinal movement. The rotation of the coupling socket 34 can be facilitated by the use of a suitable lubricant system, as discussed above. The coupling socket 34 fits over and meshes with the propelling gear when the dosating unit is fully inserted into the recess 12 of the pocket inhalator device 2. In operation, the propelling power transferred to the coupling socket 34 via the gear 55 is transformed into rotational movement of the connecting rod 80 and thus the spindle 72. Because the spindle 72 meshes with the fixed nut 74, the rotational movement results in the translational movement of the spindle 72 as it rotates, thereby advancing the plunger 66 longitudinally in the direction of the arrow 68. The rotatable pusher plate 76 provides an axial bearing between the rotating spindle 72 and the non-rotating plunger 66. Thus, the depicted arrangement provides a transmission mechanism for converting rotary motion applied by the motor 10, via the coupling socket 34, into translation of the plunger 66.

Transmission mechanisms other than that depicted in FIGS. 4 and 5 can be used to convert rotary motion of the motor 10 into translational motion of the plunger 66. For example, FIG. 6 shows a transmission mechanism with a hollow connecting spindle 72' that is mounted to the housing section 36' by roller bearings 90. In this embodiment, the central bore 78' of the spindle 72' is threaded, and meshes with cooperating thread 91 on a connecting rod 80'. The connecting rod 80' has a spindle section 93 that passes through a section 83 of the housing 36' that allows longitudinal movement of the connecting rod 80' but prevents rotation also at its longitudinal axis. The drive coupling member 34' in this embodiment constitutes a face gear that provides a one-way clutch with a cooperating face gear constituting the driving coupling member in the device. In the embodiment of FIG. 6, rotation of the connecting spindle 78' propels the connecting rod 80' axially and thus drives the plunger 66.

One skilled in the art will appreciate in view of this disclosure that still other transmission mechanisms may be used to convert the rotary movement of motor 10 into translational movement of plunger 66 without undue experimentation.

The housing cover 38 of the dosating unit 14 can assume either of two distinct positions when it is attached to the housing 36. FIG. 4 shows the cover in a first position, in which the dosating unit can be stored indefinitely. In this position, the housing cover 38 sits on the housing 36 without the fluid pipe 40 having pierced the lid 62 of the glass cartridge 58. Thus, the medicament in the cartridge 58, once sterilized, will remain sterile for an extended period of time, even though it has been loaded into the dosating unit 14.

The first, extended-storage position is realized by providing at the upper edge of the housing 36 a ring-shaped pawl 82 extending around the rim of the housing 36. The cover 38 has a cooperating outer recess 84 at its rim. The outer recess 84 is formed by a flange that extends around the circumference of the cover 38 so that the inclined surface of the pawl 82 can ride over the non-recessed portion between the outer recess 84 and the lower or bottom edge 38*a* of the cover 38 and then click lockingly into place in the outer recess 84.

The second, operative position, of the housing cover 38 relative to the housing 36 is shown in FIG. 5. In this case, the inlet end of the fluid pipe 40 has pierced the lid 62 of the glass cartridge 58, so that linear translation of the plunger 66 will force the liquid medicament through the pipe 40. Preferably, the inlet end of the pipe 40 is cut off at an angle to form a sharp edge that easily slices through the lid 62. The cover 38 is held in the second position on the housing 36 by an inner recess 86 on the cover 38, where the inclined outer surface of the pawl 82 can ride over the non-recessed portion between the outer recess 84 and the inner recess 86 and then click lockingly into place in the inner recess 86. The dosating unit housing 36 preferably has one or more, more preferably about four, longitudinal slots 85 that permit sufficient deformation of the housing for insertion into the recesses 84 and 86.

In alternative embodiments of the present invention, the pawl 82 and recesses 84 and 86 could be arranged with pawls on the cover 38 and a recess or shoulder on the housing 36. Either way, the location of the inner shoulder or pawl at a more rigid portion of the housing cover 38 will prevent ready removal of the cover once it is in its operative position and fix the position of the housing 36 relative to the cover 38.

The dosating unit 14 is typically made and sold with the cover 38 in the first position, as shown in FIG. 4. To assemble the dosating unit, the glass ampoule 58 is inserted into the housing 36 with the spindle 72 in its withdrawn position, as shown in FIG. 4. The cover 38 is then placed on the housing 36 until the pawl 82 comes to rest in the outer recess 84.

To use the atomizing device of the present invention, the patient first opens the sealed dosating unit package and inserts the dosating unit 14, with the cover 38 in the first position, into the recess 12 in the device housing 14 (see FIGS. 1 to 3). Then, the patient presses down on the housing cover 38 to cause the pawl 82 to translate to the inner recess 86 and at the same time cause the sharp inlet end of the tube 40, disposed in the opening of the metal cap 64, to pierce the lid 62 and enter the internal space of the cartridge 58. The same action positively connects the splined coupling socket 34 to the propelling gear 55. Alternatively the patient may place the dosating unit 14 in its second or operative position by pressing down on the cover 38 and the bottom of the housing 36 until the inner recess 86 is engaged by the pawl 82, followed. Then the unit may be inserted into the recess 12.

The configuration of the housing 36 closely matches the shape of the upper portion of the recess 12 to hold the dosating unit 14 in place in the housing 4 by the friction between the outer surfaces of the housing 36 and the inner surfaces of the upper portion of the recess 12. To that end, the housing 36 preferably has small ribs 98 (see FIG. 4) that bear against the inner surface of the recess 12. This has the added advantage of precisely locating the delivery outlet of the tube 40 relative to the piezoelectric element 26 for reasons discussed in more detail below. The dosating unit 14, which can be further secured in the housing by a suitable snap detent system (for example, a small protuberance on the housing cover 38 that fits into a mating depression in the recess 12 (not shown)), is thus securely held in place for use of the device, while also being easily removable for replacement by a fresh dosating unit 14 when the medicament is used up or by a different dosating unit 14 for dispensing a different medication.

To dispense medicament once the dosating unit 14 is in place in its operative position, the patient puts the mouthpiece 5 to his mouth, presses the activation button 22, which energizes the motor 10 and the piezoelectric element 26, through the batteries of the accumulator system 8 and under the control of the circuitry 6, as explained in more detail below. When the motor 10 rotates, it drives the propelling gear 56, which in turn rotates the mating splined coupling socket 34 and the connecting rod 80 and, in turn, the spindle 72. That pushes the plunger 66 in the direction of the arrow 68 and forces the medicament through the pipe 40. Each operation of the activation button 22 forces a predetermined, precisely metered amount of medicament into the pipe 40 and onto the atomization surface 28 for atomization. The patient thus inhales the atomized medicament through the mouthpiece 5.

Medicaments for use according to the invention include any medicament capable of administration by inhalation and capable of being dissolved, dispersed or suspended in a liquid medium. Such solutions, dispersions or suspensions should be capable of passage through the pipe 40 and any valve 42 and atomization on the atomization surface 28 without significant adverse effect on the relatively consistent flow of medicament and delivery thereof to the atomization surface. Such medicaments include drugs for use in the prophylactic or remedial treatment of reversible obstructive airways disease. Specific medicaments which may be used with the present invention include salts of cromoglycic acid (for example, cromolyn sodium), salts of nedocromil (for example, nedocromil sodium), inhaled steroids such as beclomethasone dipropionate, tipredane, budesonide, triamcinolone acetonide and fluticasone, anticholinergic agents such as ipratropium bromide and bronchodilators (for example, salmeterol, albuterol (salbutamol), reproterol, terbuteline, isoproterenol (isoprenaline) and fenoterol, and salts thereof). If desired a mixture of medicaments, for example, a mixture cromolyn of sodium and a bronchodilator, such as albuterol, reproterol, isoprenaline, terbuteline, fenoterol, or a salt of any one thereof, may be used. Other combinations, such as ipatropium bromide and a bronchodilator, may also be used.

Other medicaments that may be mentioned include antihistamines (for example, elemastine), pentamidine and salts thereof, acetyl-β-methycholine bromide, peptide hormones (for example, insulin and amylin), bradykinin antagonists, PLA inhibitors, PAF antagonists, lipoxygenase inhibitors, leukotriene antagonists, CNS active drugs (for example NMDA antagonists, glutamate antagonists and CCK agonists and antagonists), antibiotics, such as macrolide compounds (for example, rifampin) and structurally related compounds, enzymes, vitamins, vaccines (for example, MMR vaccine and polio vaccine), and vectors for gene therapy (for example, plasmids containing genes intended to correct genetic disorders such as cystic fibrosis).

The device as described above has numerous advantages.

First, it enables precisely metered doses of medicament to be efficiently atomized, thus minimizing waste. This is because the translating-piston dosating arrangement of the present invention readily lends itself to efficient, precision operation for many reasons.

Initially, the piston 66 and ampoule 58 are designed to minimize friction between them while still maintaining a very effective seal. This is accomplished both by maintaining the ampoule cross-section diameter as true to round as possible and using the configuration of the plunger 66 as shown in FIGS. 6A and 6B, which maximizes the effectiveness of the seal without unduly increasing friction. The plunger configuration according to the present invention also reduces mechanical hysteresis by reducing friction and at the same time making the plunger 66 as rigid as possible. Thus, the plunger 66 is deformed very little as it is forced along the walls of the ampoule 58 by the pusher 76. Therefore, dosage errors caused by deformation and subsequent recovery of the plunger 66 are avoided using the preferred plunger configuration.

The low friction and precise operation provided by the plunger 66 in turn permit use of a motor 10 with low power requirements, which enables a reduced-size motor 10 to provide the motive force for the plunger 66. That is extremely important because it enables the device 2 to be made compact and thus makes it possible for a patient to have the device 2 at hand at all times. When used with a DC motor 10 having Hall sensors to indicate rotor position, the dosating unit 14 of the present invention provides extremely accurate dosages and enables direct dosage control using digital metering circuitry. Moreover, the unique driving system of the dosating unit 14 enables gear ratios to be chosen so that a particular amount of motor rotation will provide a known amount of piston travel, and thus simplify dose metering. This is significant because of the power requirements of the piezoelectric atomizer 26, which are discussed in more detail below.

Aside from those operational advantages, an advantage from a handling standpoint is afforded by the provision of the housing cover 38 with its first position for extended storage and its securely-held second position for operation. It is not as critical that the cover 38 be securely held during storage since the cartridge's diaphragm seal will not yet be breached at that time. However, once the dosating unit is in its operative configuration, it is important for safety reasons that the patient not be able to take off the cover and expose the medicament to contamination. For example, the cover-locking arrangement ensures that the dosating unit remains intact if the patient removes it from the device 2 to insert another dosating unit 14 containing a different medication. It also ensures that the patient cannot readily insert a different medicament ampoule 58 into the dosating unit 14, which could present patient safety issues from several standpoints.

The placement of the delivery outlet 42 of the dosating unit 14 relative to the atomization surface 28 is described in connection with FIGS. 7A and 7B which are, respectively, an enlarged front view and an enlarged side view of the atomization surface 28 with the pipe 40 having a valve or nozzle 42 on the outlet in place, after the dosating unit 14 is inserted in the recess 12 and the cover 38 is pressed down to assume its operative position (FIG. 5). The location of the delivery outlet 42 relative to the atomization points is assured by providing mating datum surfaces in three orthogonal planes on the dosating unit 14 and on the device housing 4, and by locating the outlet precisely relative to the datum points on the dosating unit 14 and locating the atomization surface 28 precisely relative to the datum point on the device 2. The housing 36 of the dosating unit 14, which is substantially fixed in position relative to the cover 38 and the pipe 40 by the pawl 82 and the inner recess 86, and therefore the delivery outlet of the tube 40, may be located in the x and z directions shown in FIGS. 7A and 7B by ribs 98 on the housing 36 and the inner surface of the recess 12. The nozzle is located vertically (in the y direction) by the bottom surface 38*a* of the cover 38 as it bears on the shoulder 44 formed by the top of the dosating unit housing 36. In other words, locating the outlet 42 precisely relative to three orthogonal datum points on the dosating unit 14, and locating the atomization surface 28 precisely relative to three mating orthogonal datum points on the device housing 4, will provide the necessary precision location of the outlet 42 relative to the piezoelectric element 26 when the dosating unit 14 is in its operative position in the device 2.

Figure 7B:
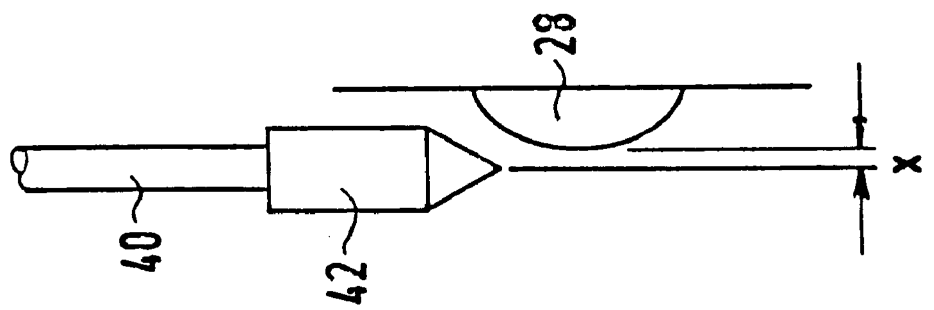
FIGS. 7A and 7B illustrate the relationship of a delivery outlet of the dosating unit when it is in an operative position in the device in FIGS. 1 to 3.
Figure 7A:
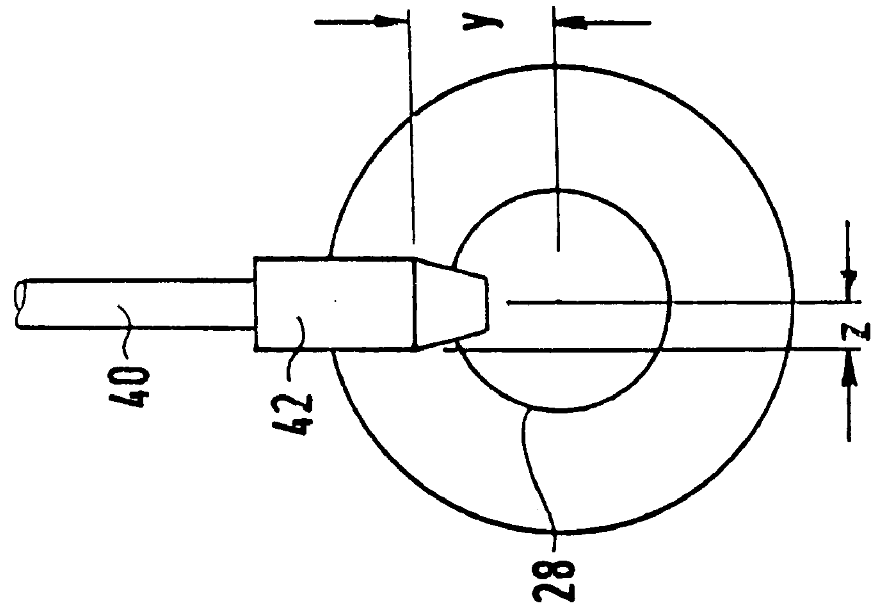

Referring to FIGS. 7A and 7B, the valve 42 is seen in place relative to the atomization surface 28 from the front (FIG. 7A) and the side (FIG. 7B). The atomization surface 28 is provided in accordance with the teachings of EP 0 689 879 A1, which is parallel to a U.S. application by Klaus van der Linden, Olaf Haack and Randolf Mock, filed Jun. 29, 1995, claiming priority of German application No. P 44 22 822.8 of Jun. 29, 1994, and incorporated herein by reference. The structure shown in that application is particularly suited to atomizing liquid for administering medication and thus it is contemplated that it will be used in the inhalator device 2 herein. However, as that application points out, it is important to proper operation that the liquid to be atomized be delivered to the highest point of the atomization surface 28 in order to properly atomize the liquid for medicament delivery.

FIGS. 7A and 7B show the location of the valve 42 relative to the atomization surface 28 in the three orthogonal directions, x, y and z. Those distances are typically measured between the point at which the liquid issues from the valve 42 to the highest point on the atomization surface 28. The most critical dimension for locating the valve opening relative to the atomization surface is in the y direction. The distance z should be as close to zero as possible. (The valve is shown in FIG. 7A offset by a distance z solely to illustrate the orientation of the z direction.) In the x direction the distance is typically 0.1 to 0.5 mm and in the y direction the distance should be 0.1 mm to 2.0 mm.

FIGS. 8A to 8D show various embodiments of the valve 42 at the end of the tube 40.

Figure 8F:
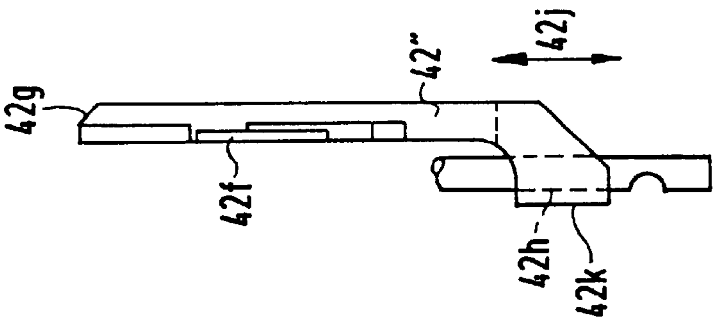
FIG. 8F is a side view of the embodiment in FIG. 8E.
Figure 8E:
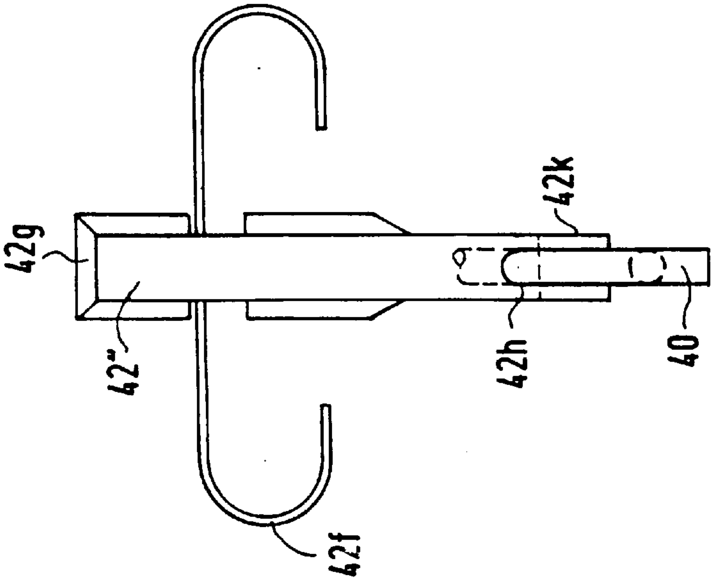
FIGS. 8A to 8C and 8E are different embodiments of valves and closures for the end of the delivery nozzle of the dosating unit.
Figure 8D:
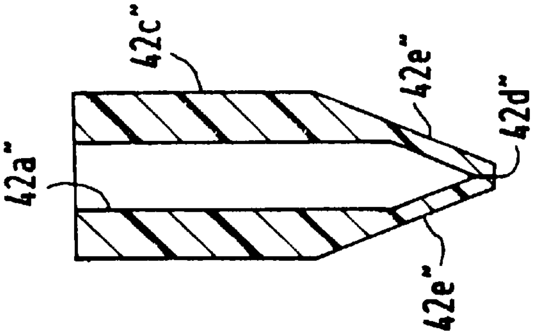
FIG. 8D is a side view of the embodiment in FIG. 8C.
Figure 8C:
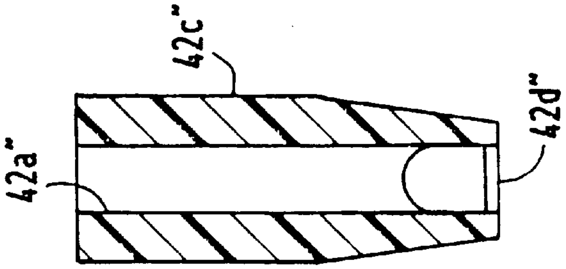
Figure 8B:
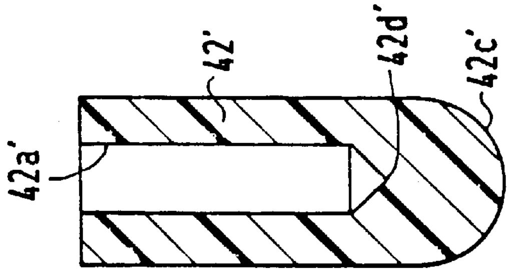
Figure 8A:
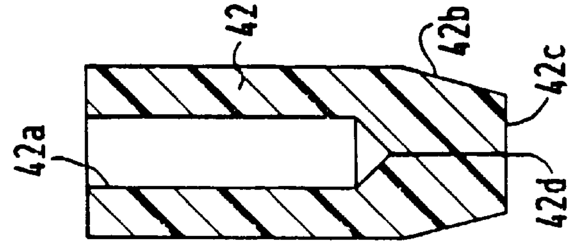

FIG. 8A is an enlarged view of the valve 42 shown in FIGS. 4 and 5. It is a sleeve comprised of a resilient material, preferably silicone rubber, with an inner bore 42*a* having a diameter slightly smaller than the outer diameter of the tube 40 so as to fit snugly and securely thereon. It has a tapered outer surface 42*b* with a flat end 42*c*. A slit 42*d* connects the flat end with the inner bore 42*a*. The slit has a length (in the direction normal to the drawing) slightly less than the diameter of the bore 42*a* and shorter than the diameter of the flat end 42*a*.

In operation, medicament liquid enters the bore and the fluid pressure created by the plunger 66 deforms the valve 42 to enable the liquid to exit the slit and deposit onto the atomization surface 28. Once the pressure is removed (that is, when the plunger 66 is no longer driven), the slit 42*d* closes to resist contamination and evaporative loss of the liquid.

The embodiment of FIG. 8B is similar to that of FIG. 8A, except that the end 42*c'* of the valve 42' is rounded and the slit 42*d'* is provided from the internal bore 42*a'* at a 45° angle to the centerline of the bore. The valve is placed on the tube 40 so that the slit is horizontal (aligned in the z direction in FIG. 7A) and facing the atomization surface 28 when the dosating unit 14 is in its operative position in the device 2.

The embodiment of FIGS. 8C and 8D is also a modified version of the embodiment in FIG. 8A, in that the end 42*c"* of the valve 42" is rectangular and the inside bore 42*a"* is enlarged all the way to the tip of the valve. This has the effect of providing two flaps 42*c"* that permit the slit 42*d"* to open and close more easily. Valve 42" can thus be specified as "flap valve".

The embodiment of FIGS. 8E and 8F is a sliding valve 42" that acts in connection with the inhaler cover 3 to open and close the pipe outlet. In this embodiment, the pipe outlet is formed on a sidewall of the pipe 40 and the valve 42" is formed with a slot or conduit 42*h* therethrough to slidingly receive the pipe 40 therein. The valve 42" can slide in the direction of arrows 42*j* from an open position (as shown) to a closed position (not shown) where an outlet cover portion 42*k* of the valve 42" covers the pipe outlet. An upper surface 42*g* of the valve 42" is shaped so as to slidingly engage an inner surface (not shown) of the cover 3 so that when the patient places the cover 3 on the device 2, the engagement of the cover 3 with the upper edge 42*g* of the valve 42" causes the valve 42" to slide down the pipe 40 to the closed position. Biasing means 42*f,* such as wire springs, are preferably used to bias the valve 42" toward the open position when the cover 3 is removed.

Different medicaments may be delivered better by different valve arrangements, which provides yet another advantage of the present invention. That is, since dosating unit 14 can be used interchangeably with different medicaments, the best valve for a given medicament can be incorporated with the dosating unit 14.

Figure 9:
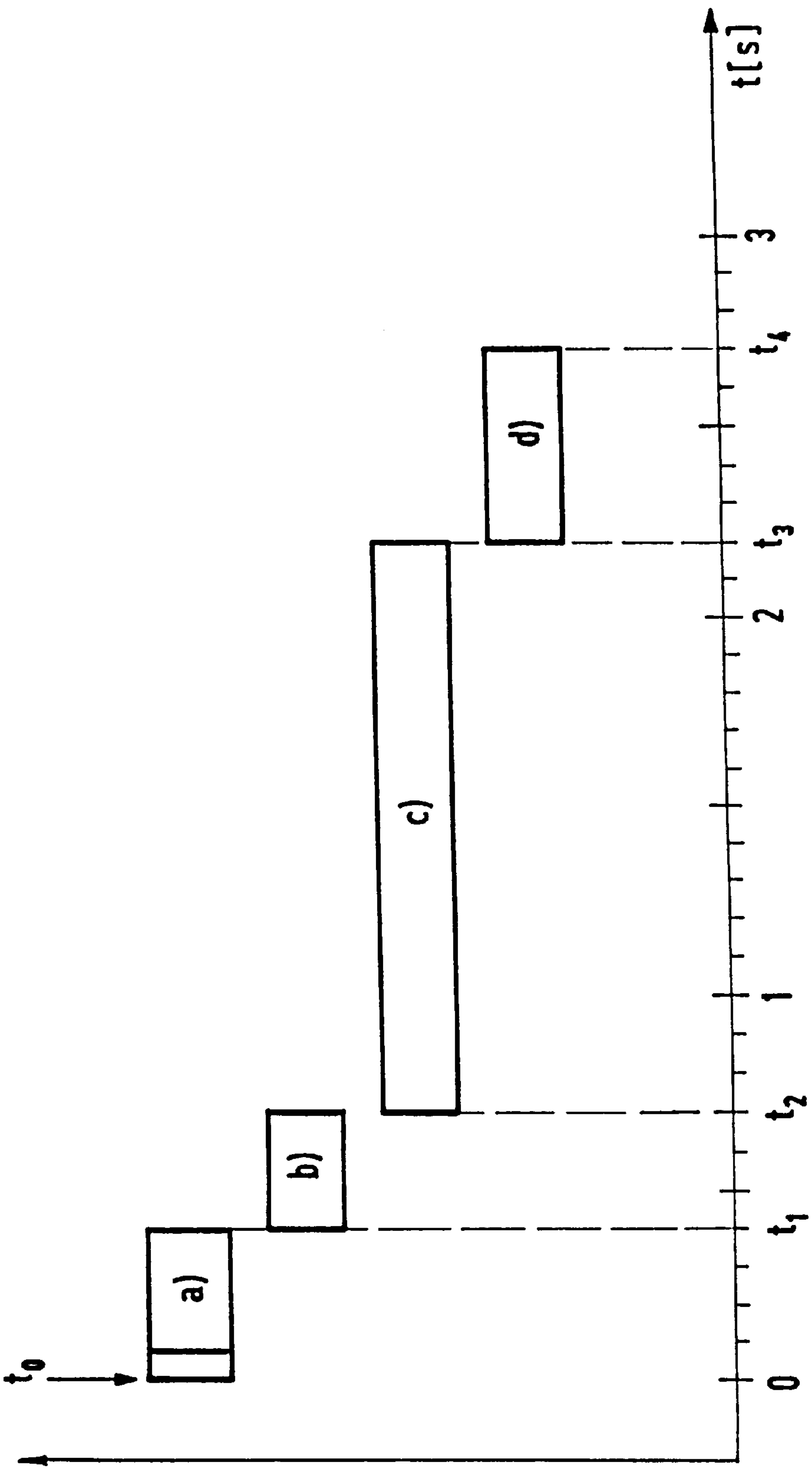
FIG. 9 is a timing diagram of the operation of the device.
Figure 10:
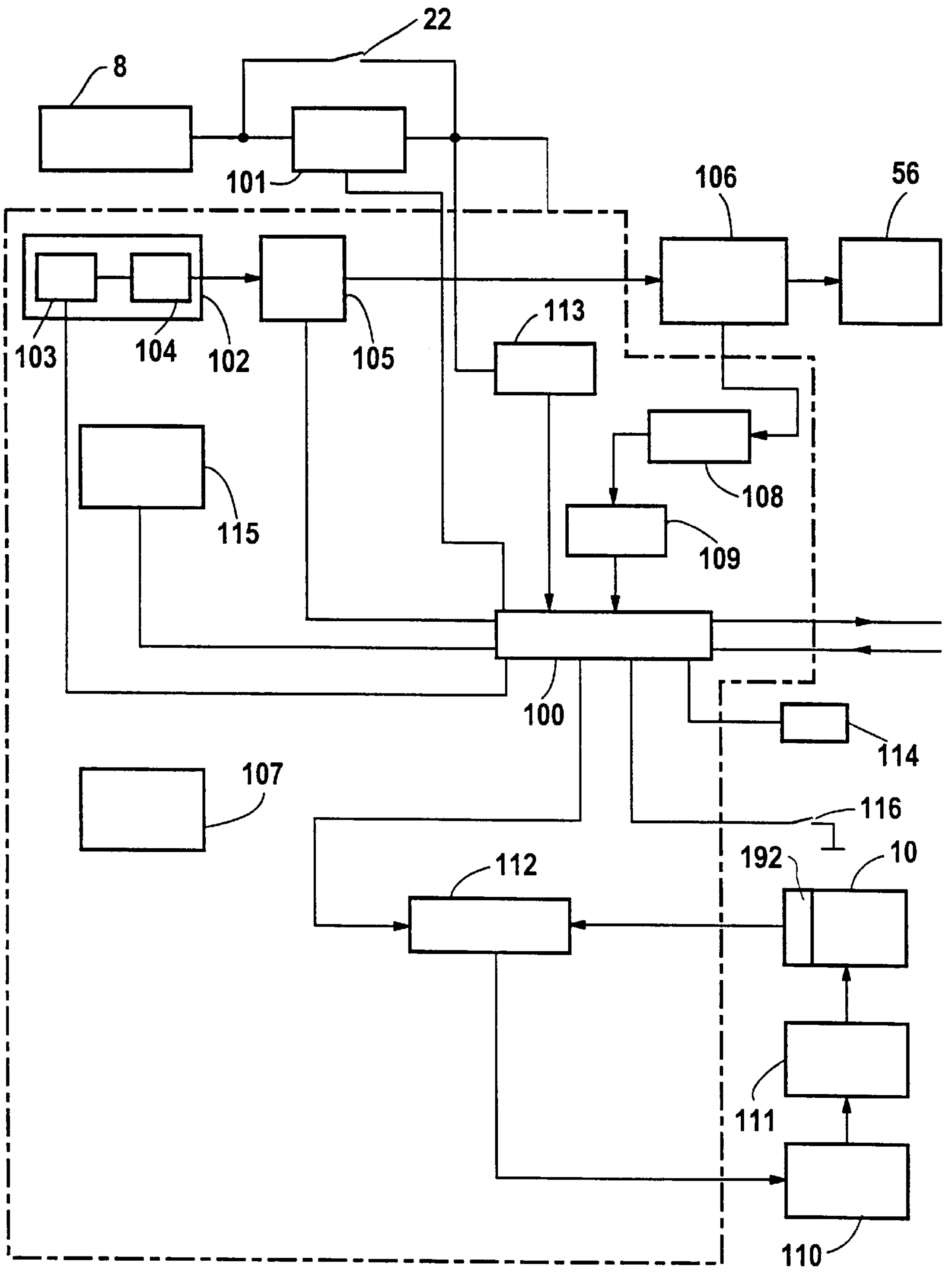
FIG. 10 is a block diagram of one embodiment of an electronic circuit in accordance with the present invention.

FIG. 9 is a timing diagram showing the operation of the motor 10 and piezoelectric element 26 as controlled by the electronic circuit 6, which is schematically drawn as a block diagram in FIG. 10. The time t in seconds is shown on the abscissa. The sequence of operation is represented by four steps a to d. The operation begins with activation of the activation element 22 (which, if it is a button, is pushed by the patient). The activation element 22 can be sealed to maintain the waterproof characteristics of the device 2. In a preferred embodiment the activation element 22 is sealed by a silicone rubber cap. By pressing of the activation element 22, a power supply with an output voltage of 9 V to 14 V is switched on. The power supply is provided as an accumulator system 8 including nine batteries. With a self-held relay 101 the power supply of the electronic circuit 6 is maintained automatically by shortcutting the activation element 22 until a controller 100 opens the relay 101.

First, step a, which is a self-cleaning process of the piezoelectric element 26, between to (pressing of the element 22) and $t_1$, lasts for a period of approximately 0.1 seconds to 1 second, preferably 0.4 seconds, and involves energization of the piezoelectric element 26 without concomitant fluid delivery, meaning without rotation of the motor 10. During this operation, any residual medication that may be present from a previous dosing operation are safely removed so that the impedance behavior of the piezoelectric element 26 is stabilized. This self-cleaning process is done by providing a signal having a frequency within a range of 1.5 MHz to 1.6 MHz to the piezoelectric element 26. Generally, the provided frequency depends on the characteristics of the piezoelectric element 26. The frequency is produced by a frequency-synthesizer 102, which has a voltage controlled oscillator (VCO) 103 and a programmable frequency-divider 104. It is imaginable to produce the frequency by other electronical means. A first amplifier 105, which can be switched off and on via the controller 100, amplifies pulses from the frequency-synthesizer. The amplified pulses drive the piezoelectric element 26 via a first power-stage 106.

The cleaning operation starts after 50 ms at high frequency to initialize the VCO 103. Subsequently, the controller decreases and increases the frequency via the divider 104 within the frequency range with steps of 1 kHz, whereby the number of steps and the time per step are programmable. At $t_1$ the controller 100 switches off the first amplifier 105, finishing the cleaning operation.

As an internal clock for time reference the electronic circuit 6 includes a crystal oscillator 107 with a frequency of 4.096 Mhz.

Then, step b is performed between $t_1$ and $t_2$, over a period of approximately 0.1 seconds to 1 second, preferably 0.3 seconds, to search the best frequency for the piezoelectric element 26. The controller 100 switches on the first amplifier 105 and again via the divider 104 the frequency is decreased and increased within the possible frequency range of the frequency synthesizer 102. With a feedback via a second amplifier 108, which is connected to the first power stage 106, and an A/D-converter 109, a working point of the piezoelectric element 26, involving a particularly low power consumption, is established by measuring the power consumption and comparing the actual value with the value of the preceding step. The absolute minimum of power consumption of the piezoelectric element 26 means the resonance frequency. This frequency will be stored in the controller for the next operational step. The piezoelectric element 26 always works with this frequency, which results in extremely economical use of the energy stored in the accumulator system 8. At $t_2$ the controller 100 switches off the first amplifier 105, finishing step b.

In the following step c, between $t_2$ and $t_3$, lasting for 0.5 seconds to 5 seconds, preferably 1.5 seconds, the piezoelectric element 26 is excited by switching on the first amplifier 105 and at the same time the motor 10 is energized by the controller 100 via a second power stage 110 to effect a continuous delivery of the medicament to the atomization surface 28. The fluid hitting the atomization surface 28 is thus atomized to a lung-accessible aerosol and can be inhaled via the mouthpiece 5.

During this time, the plunger 66 is moved via the motor 10 in the direction of the arrow 68 (see FIG. 4) to propel the medicament through the pipe 40. For high moving precision, the motor 10 is a DC-motor, which is driven by electrical pulses of a pulse-generator 111 which works regulated by the controller 100 at a frequency of approximately 1200 Hz. Alternatively, the motor 10 is a stepping-motor. The resulting fluid pressure opens the valve 42 and the liquid is supplied directly and continuously onto the atomization surface 28. The construction of the dosating unit 14 as well as the regulation of the motor-speed, which is described in more detail below, is such that an extremely precise amount of medicament can be expelled at a finely controlled rate of flow that matches exactly the characteristics of the atomization surface 28 and the piezoelectric element 26. As a result, the medicament liquid is atomized efficiently and consistently, thus providing optimum delivery of the medicament. Accordingly, medication is delivered without the waste incidental to prior delivery systems that required more than the necessary amount to be made available just to ensure that an efficacious dose reached the patient's lungs.

At $t_3$, the predetermined dosage amount has been delivered and during step d between $t_3$ and $t_4$, approximately 0.2 seconds to 5 seconds, preferably 0.5 seconds, the piezoelectric element 26 is excited at the working point without further delivery of fluid. In this manner, any medicament fluid that remains on the piezoelectric element 26 is safely atomized and the atomization surface 28 is cleaned. At $t_4$, the power supply is automatically switched off.

The electronic circuit 6 furthermore is designed such that any activation of the activation element 22 is ignored during steps a to d, meaning during the time $t_0$ to $t_4$. In this way incorrect dosages or malfunctions can be avoided.

The electronic circuit 6 furthermore is designed such that a warning signal is generated if the voltage of the batteries of the accumulator system 8 falls below a given minimum voltage and/or if the amount of medicament in the glass ampoule 58 has reached a minimum level or is completely empty and/or if a relatively large increase of friction has occurred in the motor 10 and/or in the dosating unit 14. Such a warning signal may be the illumination of a light-emitting diode or an audible alarm in a warning device 214. For generation of the warning signal, the electronic circuit 6 includes a plurality of sensors. The electronic circuit 6 includes a voltage comparator 113 that compares the available voltage with a minimum voltage and indicates that the available voltage has reached or gone below this minimum voltage. And where the housing 36 is light-transmissive, it is possible to use a light-emitting diode 90 and a photosensor 92 to detect the state of the glass ampoule 58, whereby interruption of the light path between the diode 90 and the photosensor 92 by the plunger 66 is interpreted as an indication that emptying of the glass ampoule 58 is imminent.

To get an extremely precise amount of expelled medicament or to detect a comparatively large increase of friction in the motor 10 and/or in the dosating unit 14, the current motor speed is controlled via a motor sensor 92 and an electrical phase comparator 112 on the electronic circuit 6. The motor sensor 92 is an impulse generator, which is mounted on the motor shaft, so the impulse-frequency is ideally identical with the driving frequency. The impulse-frequency is compared via the phase comparator 112 with the driving frequency of the DC-motor 10. If the actual impulse-frequency of the motor 10 differs from the driving frequency, the controller regulates the driving frequency via the pulse generator 111 in such a way that the impulse-frequency of the motor 10 is exactly 1200 Hz. In case of a too-large deviation of the actual rotational angle from the desired rotational angle, the warning device 214 is energized indicating that the user of the pocket inhalator device should change the dosating unit 14, or possibly have the motor 10 examined.

To differentiate those possible causes of a warning signal, the warning device 114 can be provided as a unit of three light-emitting diodes of differing colors and/or an audible alarm could be provided by a buzzer array to generate notes of different frequencies. The user therefore knows either to load new batteries into the accumulator device 8 (or recharge the old batteries), and/or to change the dosating unit 14 owing to an imminent or complete emptying, and/or to change the dosating unit 14 owing to a comparatively large increase of friction, and/or to completely change the device 2 owing to a comparatively high increase in friction in the motor 10.

The electronic circuit 6 furthermore is so provided that depending upon the available voltage from the accumulator system batteries the piezoelectric element 26 and the motor 10 can either be supplied by a different power supply or by public utility current supplied through the socket 20.

Furthermore, the electronic circuit 6 preferably includes a 34 bit PROM-cell 115 for factory settings. Additionally, the controller may be connected to an optional start switch 116, which can be breath actuated.

To enable factory tests, parameter settings and the like with usual computer hardware, a serial port 200, symbolized by arrows, is also provided. Via that serial port 200, the controller 100 can be connected to such hardware.

In general, it must be emphasized that the electronic circuit 6, which is drawn schematically in FIG. 10, could alternatively be provided with other electronical components, such as a programmable computer chip on board, including all the above described features.

It will be appreciated that even though the present invention has been described in terms of a medication-delivery system, it has wider application as an atomizer for any suitable purpose, particularly in, but not limited to, those cases in which a precise amount of fluid is to be atomized and/or maintaining antiseptic conditions is important.

In general, it is to be understood that this invention is not limited to the precise embodiments discussed above, and that various changes and modifications in such embodiments, in addition to those already specifically noted, can be effected without departing from the spirit or scope of the invention, which is intended to be defined solely by the following claims.

We claim:

1. A dosating unit removably mountable to an atomizing device, said unit comprising:

an elongated first section for accepting therein an ampoule containing liquid to be delivered to the atomizing device through a delivery pipe; and a second section secured to said first section and including a drive mechanism for cooperating with a plunger in the ampoule to cause said plunger to translate within the ampoule to force liquid therein through said liquid delivery pipe, a transmission mechanism for converting rotary motion applied thereto into translating motion applied to said drive mechanism and a driving member for applying rotary motion from a motor in the device to said transmission mechanism.

2. A dosating unit according to claim 1, wherein said second section is elongated and said elongated first section and said elongated second section are integrated into a housing and are circularly cylindrical, with said first section having a cross-sectional diameter greater than said second section.

3. A dosating unit according to claim 1, wherein said transmission mechanism includes a hollow spindle threaded into a fixed nut and said driving mechanism includes a connecting rod disposed within said spindle and connected to said driving member for rotation therewith, said spindle being translatable relative to said connecting rod so that rotation of said connecting rod causes said spindle to translate by rotation within said fixed nut.

4. A dosating unit according to claim 3, wherein a pusher member is connected to said spindle for rotation relative thereto.

5. A dosating unit according to claim 4, wherein said pusher member has a bearing surface for bearing against the plunger in the ampoule along a substantial portion of the diameter of the plunger.

6. A dosating unit according to claim 3, wherein said driving member comprises a driving cog for meshing with a drive spline operatively connected to a motor in the device when said dosating unit is in an operative position in the device.

7. A dosating unit according to claim 1, wherein said transmission mechanism includes a hollow spindle with a threaded central bore, said spindle being mounted for rotation within said second section for rotation by said driving member, and said drive mechanism includes a connecting rod with a threaded portion cooperating with said threaded central bore of said hollow spindle, said connecting rod being restrained from rotation so that rotation of said spindle causes said connecting rod to translate.

8. A dosating unit according to claim 7, wherein said driving member is formed at an end of said spindle.

9. A dosating unit removably mountable to an atomizing device, said dosating unit comprising:

a housing for accepting therein a cartridge containing a liquid to be delivered to the atomizing device;

a fluid delivery pipe having an inlet into which liquid in the cartridge is introduced when said fluid delivery pipe is in an operating position on said housing, and an outlet for delivering fluid to an atomizing surface of the atomizing device; and positioning means on said housing for cooperating with the device to locate said outlet precisely in three orthogonal directions relative to the device, wherein said outlet is precisely located relative to said positioning means so that said outlet will be precisely located in the device when the dosating unit is in the operative position thereof.

10. A dosating unit according to claim 9, wherein said positioning means comprises three datum surfaces in respective orthogonal planes for cooperating with corresponding datum surfaces precisely located relative to the atomizing surface in the device, said outlet being precisely located relative to each said datum surface to precisely locate said outlet relative to the atomizing surface when the dosating unit is in an operative position in the device.

11. A dosating unit according to claim 10, wherein said fluid delivery pipe is integrally molded in place with a molded plastic cover for said housing.

12. A dosating unit according to claim 9, further including a valve disposed on said delivery pipe to form said outlet, wherein said valve opens to permit liquid to escape said delivery pipe when pressure is applied to the liquid and closes to resist contamination of the liquid when no pressure is applied to the liquid.

13. A dosating unit according to claim 12, wherein said valve comprises a rubber sleeve having an integral bore fitted over an end of said delivery pipe and a slot forming said outlet in an end of said rubber sleeve and connecting said internal bore with said end.

14. A dosating unit according to claim 13, wherein said rubber sleeve has a round cross-section with a tapering portion at said end ending in a flat surface having said slot therein.

15. A dosating unit according to claim 13, wherein said rubber sleeve has a round cross-section with a rounded end having said slot therein disposed at a 45° angle to a centerline of said internal bore.

16. A dosating unit according to claim 13, wherein said rubber sleeve has a round cross-section in a portion thereof fitted over said delivery pipe and a tapered portion with flat sides ending in a flat surface having said slot therein, said internal bore extending into said tapered portion.

17. A dosating unit according to claim 9, further including a valve mounted on said fluid delivery pipe for movement between an open position permitting liquid to be delivered from said outlet and a closed position covering said outlet.

18. A dosating unit according to claim 17, wherein said outlet is in a side of said fluid delivery pipe and said valve is slidingly mounted on said fluid delivery pipe for covering said outlet in the closed position and exposing said outlet in the open position, said valve further including spring means for biasing said valve in the open position and a camming surface for cooperating with an inhaler cover to slide said valve against said spring means into the closed position when the inhaler cover is placed on the inhaler.

19. A dosating unit removable mounted to an atomizing device, said unit comprising:

a housing accepted by the atomizing device;

an ampoule containing a medicament liquid to be supplied to the device for atomization, said ampoule being contained in said housing; and a housing cover disposed on said housing and having a fluid delivery pipe for piercing said ampoule, said cover and said housing including cooperating securing means for securing said cover to said housing in a first position wherein said fluid delivery pipe does not pierce said ampoule and a second position wherein said fluid delivery pipe pierces said ampoule, said securing means resisting movement of said cover from said second position toward said first position.

20. A dosating unit according to claim 19, wherein said cover translates relative to said housing from said first position to said second position, said securing means including a first shoulder and second shoulder on said cover and a locking pawl on said housing for cooperating with said first and second shoulders.

21. A dosating unit according to claim 19, further including a drive mechanism in said housing for cooperating with a plunger in said ampoule for translating said plunger to force liquid therein through said delivery pipe.

22. A dosating unit according to claim 21, wherein said plunger is solid rubber with two sealing lips for cooperating with an internal wall of said ampoule to provide a liquid-tight seal between said plunger and said ampoule.

23. A dosating unit according to claim 22, wherein said sealing lips are formed by a recessed portion therebetween and have rounded edges for reducing friction between said sealing lips and said internal wall of said ampoule.

24. A dosating unit according to claim 23, wherein said plunger includes a pair of opposed, raised arc-shaped members having a space therebetween along a diameter of said plunger, and said drive mechanism includes a plunger pusher for bearing against said plunger.

* * * * *